United States Patent [19]
Harrison et al.

[11] Patent Number: 6,133,255
[45] Date of Patent: Oct. 17, 2000

[54] TRICYCLIC PYRIDONE ANALOGUES AS GABA-A RECEPTOR LIGANDS

[75] Inventors: Timothy Harrison, Great Dunmow; Richard Thomas Lewis, Bishops Stortford; Christopher Richard Moyes, Sawbridgeworth; Alan Nadin, Cambridge; Andrew Pate Owens, Huntingdon, all of United Kingdom

[73] Assignee: Merck Sharp & Dohme Limited, Hoddesdon, United Kingdom

[21] Appl. No.: 09/381,988

[22] PCT Filed: Apr. 22, 1998

[86] PCT No.: PCT/GB98/01167

§ 371 Date: Sep. 27, 1999

§ 102(e) Date: Sep. 27, 1999

[87] PCT Pub. No.: WO98/50384

PCT Pub. Date: Nov. 12, 1998

[30] Foreign Application Priority Data

May 1, 1997 [GB] United Kingdom .................. 9708945

[51] Int. Cl.[7] ..................... C07D 471/14; C07D 471/04; A61K 31/435
[52] U.S. Cl. ............... 514/214.01; 540/586; 514/214.02
[58] Field of Search ..................................... 540/586, 579; 514/217, 214.01, 214.02

[56] References Cited

U.S. PATENT DOCUMENTS

| | | | |
|---|---|---|---|
| 4,735,940 | 4/1988 | Fischer et al. | 574/212 |
| 4,855,297 | 8/1989 | Fischer et al. | 514/248 |
| 4,889,848 | 12/1989 | Fischer et al. | 514/212 |
| 4,889,854 | 12/1989 | Widmer | 514/228.2 |
| 5,036,066 | 7/1991 | Fischer et al. | 514/211 |
| 5,082,842 | 1/1992 | Widmer | 514/248 |
| 5,114,934 | 5/1992 | Fischer et al. | 514/212 |
| 5,143,912 | 9/1992 | Burner et al. | 514/210 |
| 5,258,387 | 11/1993 | Burner et al. | 514/291 |
| 5,321,021 | 6/1994 | Fischer et al. | 514/211 |

OTHER PUBLICATIONS

Bayley, et al. *J. Pschopharmacol.*, 10: 206–213 (1996).
Bristow, et al., *J. Pharmacol. Exp. Ther.*, 279:492–501 (1996).
Dawson, et al., *Psychopharmacology*, 121: 109–117 (1995).
Wafford, et al., *Mol. Pharmacol.*, 50:670–678 (1996).

*Primary Examiner*—Mukund J. Shah
*Assistant Examiner*—Hong Liu
*Attorney, Agent, or Firm*—Shu M. Lee; David L. Rose

[57] ABSTRACT

Tricyclic pyridin-2-one analogues which are ligands for $GABA_A$ receptors, are useful in the therapy of deleterious mendtal states, and are represented by the formula:

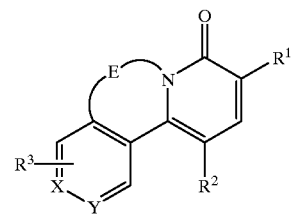

7 Claims, No Drawings

TRICYCLIC PYRIDONE ANALOGUES AS GABA-A RECEPTOR LIGANDS

The present invention relates to a class of fused tricyclic compounds based on a substituted pyridone ring, and to their use in therapy. More particularly, this invention is concerned with tricyclic pyridin-2-one analogues which are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six $\alpha$ subunits, four $\beta$ subunits, three $\gamma$ subunits, one $\delta$ subunit, one $\epsilon$ subunit and two $\rho$ subunits.

Although knowledge of the diversity of the $GABA_A$ receptor gene family represents a huge step forward in our understanding of this ligand-gated ion channel, insight into the extent of subtype diversity is still at an early stage. It has been indicated that an $\alpha$ subunit, a $\beta$ subunit and a $\gamma$ subunit constitute the minimum requirement for forming a fully functional $GABA_A$ receptor expressed by transiently transfecting cDNAs into cells. As indicated above, $\delta$, $\epsilon$ and $\rho$ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one $\alpha$, one $\beta$ and one $\gamma$ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, $\alpha 1\beta 2\gamma$, $\alpha 2\beta^{2/3}\gamma 2$, $\alpha 3\beta\gamma^{2/3}$, $\alpha 2\beta\gamma 1$, $\alpha 5\beta 3\gamma^{2/3}$, $\alpha 6\beta\gamma 2$, $\alpha 6\beta\delta$ and $\alpha 4\beta\delta$. Subtype assemblies containing an a1 subunit are present in most areas of the brain and are thought to account for over 40% of $GABA_A$ receptors in the rat. Subtype assemblies containing $\alpha 2$ and $\alpha 3$ subunits respectively are thought to account for about 25% and 17% of $GABA_A$ receptors in the rat. Subtype assemblies containing an $\alpha 5$ subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the $\alpha 1$ subunit in combination with a $\beta$ subunit and $\gamma 2$. This is the most abundant $GABA_A$ receptor subtype, and is believed to represent almost half of all $GABA_A$ receptors in the brain.

Two other major populations are the $\alpha 2\beta\gamma 2$ and $\alpha 3\beta\gamma^{2/3}$ subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain $\alpha 5$-containing subtype assemblies. The physiological role of these subtypes has hitherto been unclear because no sufficiently selective agonists or antagonists were known.

It is now believed that agents acting as BZ agonists at $\alpha 1\beta\gamma 2$, $\alpha 2\beta\gamma 2$ or $\alpha 3\beta\gamma 2$ subunits will possess desirable anxiolytic properties. Compounds which are modulators of the benzodiazepine binding site of the $GABA_A$ receptor by acting as BZ agonists are referred to hereinafter as "$GABA_A$ receptor agonists". The $\alpha 1$-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the $\alpha 1$ subunit. Accordingly, it is considered that $GABA_A$ receptor agonists which interact more favourably with the $\alpha 2$ and/or $\alpha 3$ subunit than with a1 will be effective in the treatment of anxiety with a reduced propensity to cause sedation. Also, agents which are antagonists or inverse agonists at $\alpha 1$ might be employed to reverse sedation or hypnosis caused by $\alpha 1$ agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia: attention deficit hyperactivity disorder; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as post-operative nausea and vomiting; muscle spasm or spasticity, e.g. in paraplegic patients; and hearing loss. Selective ligands for $GABA_A$ receptors may also be effective as pre-medication prior to anaesthesia or minor procedures such as endoscopy, including gastric endoscopy.

EP-A-0183994 relates to bi- and tricyclic pyridone derivatives which are stated to have muscle relaxant, sedative-hypnotic, anxiolytic and/or anticonvulsant activity. There is no disclosure nor any suggestion therein, however, of compounds possessing an ester or thiazole substituent at the 3-position of the pyridone ring.

The present invention provides a class of tricyclic pyridin-2-one analogues which possess desirable binding properties at various $GABA_A$ receptor subtypes. The compounds in accordance with the present invention have good affinity as ligands for the $\alpha 2$ and/or $\alpha 3$ subunit of the human $GABA_A$ receptor. The compounds of this invention may interact more favourably with the $\alpha 2$ and/or $\alpha 3$ subunit than with the $\alpha 1$ subunit. Desirably, the compounds of the invention will exhibit functional selectivity in terms of a selective efficacy for the $\alpha 2$ and/or $\alpha 3$ subunit relative to the $\alpha 1$ subunit.

The compounds of the present invention are GABA$_A$ receptor subtype ligands having a binding affinity ($K_i$) for the α2 and/or α3 subunit, as measured in the assay described hereinbelow, of 100 nM or less, typically of 50 nM or less, and ideally of 10 nM or less. The compounds in accordance with this invention may possess at least a 2-fold. suitably at least a 5-fold, and advantageously at least a 10-fold, selective affinity for the α2 and/or α3 subunit relative to the cxl subunit. However. compounds which are not selective in terms of their binding affinity for the α2 and/or α3 subunit relative to the α1 subunit are also encompassed within the scope of the present invention; such compounds will desirably exhibit functional selectivity in terms of a selective efficacy for the α2 and/or α3 subunit relative to the α1 subunit.

The present invention provides a compound of formula I, or a salt or prodrug thereof:

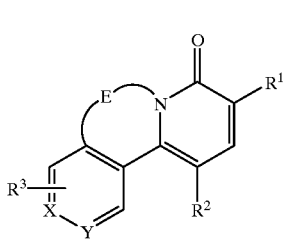

(I)

wherein

E represents —(CH$_2$)$_n$—;

n is 1, 2 or 3;

one of X and Y represents CH, nitrogen or N$^+$—O—, and the other represents CH;

R$^1$ represents methoxycarbonyl, ethoxycarbonyl, methylthiazolyl or hydroxymethylthiazolyl;

R$^2$ and R$^3$ independently represent hydrogen, hydrocarbon, a heterocyclic group, halogen, cyano, trifluoromethyl, nitro, —OR$^a$, —OCOR$^a$, —OSO$_2$R$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$, or —CONR$^a$R$^b$; and R$^a$ and R$^b$ independently represent hydrogen, hydrocarbon or a heterocyclic group.

For use in medicine, the salts of the compounds of formula I will be pharmaceutically acceptable salts. Other salts may,. however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include C$_{1-6}$ alkyl, C$_{2-6}$ alkenyl, C$_{2-6}$ alkynyl, C$_{3-7}$ cycloalkyl, C$_{3-7}$ cycloalkyl(C$_{1-6}$)alkyl, indanyl, aryl, aryl (C$_{1-6}$)alkyl, aryl(C$_{2-6}$)alkenyl and aryl(C$_{2-6}$)alkynyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include C$_{3-7}$ heterocycloalkyl, C$_{3-7}$ heterocycloalkyl(C$_{1-6}$)alkyl, heteroaryl and heteroaryl(C$_{1-6}$)alkyl groups.

Suitable alkyl groups include straight-chained and branched alkyl groups containing from 1 to 6 carbon atoms. Typical examples include methyl and ethyl groups, and straight-chained or branched propyl, butyl and pentyl groups. Particular alkyl groups are methyl, ethyl, n-propyl, isopropyl, isobutyl, tert-butyl and 2,2-dimethylpropyl. Derived expressions such as "C$_{1-6}$ alkoxy", "C$_{1-6}$ alkylamino" and "C$_{1-6}$ alkylsulphonyl" are to be construed accordingly.

Suitable alkenyl groups include straight-chained and branched alkenyl groups containing from 2 to 6 carbon atoms. Typical examples include vinyl, allyl and dimethylallyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Typical examples of C$_{3-7}$ cycloalkyl(C$_{1-6}$)alkyl groups include cyclopropylmethyl, cyclohexylmethyl and cyclohexylethyl.

Particular indanyl groups include indan-1-yl and indan-2-yl.

Particular aryl groups include phenyl and naphthyl.

Particular aryl(C$_{1-6}$)alkyl groups include benzyl, phenylethyl, phenylpropyl and naphthylmethyl.

A particular aryl(C$_{2-6}$)alkenyl group is phenylethenyl.

A particular aryl(C$_{2-6}$)alkynyl group is phenylethynyl.

Suitable heterocycloalkyl groups include azetidinyl, pyrrolidinyl, piperidinyl, piperazinyl and morpholinyl groups.

Suitable heteroaryl groups include pyridinyl, quinolinyl, isoquinolinyl, pyridazinyl, pyrimidinyl, pyrazinyl, pyranyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl(C$_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The hydrocarbon and heterocyclic groups may in turn be optionally substituted by one or more groups selected from C$_{1-6}$ alkyl, adamantyl, phenyl, halogen, C$_{1-6}$ haloalkyl, C$_{1-6}$ hydroxyalkyl, C$_{1-6}$ aminoalkyl, trifluoromethyl, hydroxy, C$_{1-6}$ alkoxy, aryloxy, keto, C$_{1-3}$ alkylenedioxy, nitro, cyano, carboxy, C$_{2-6}$ alkoxycarbonyl, C$_{2-6}$ alkoxycarbonyl(C$_{1-6}$) alkyl, C$_{2-6}$ alkylcarbonyloxy, arylcarbonyloxy, aminocarbonyloxy, formyl, C$_{2-6}$ alkylcarbonyl, arylcarbonyl, C$_{1-6}$ alkylthio, C$_{1-6}$ alkylsulphinyl, C$_{1-6}$ alkylsulphonyl, arylsulphonyl, —NR$^v$R$^w$, —NR$^v$COR$^w$, —NR$^v$CO$_2$R$^w$, —NR$^v$SO$_2$R$^w$, —CH$_2$NR$^v$SO$_2$R$^w$, —NHCONR$^v$R$^w$, —CONR$^v$R$^w$, —SO$_2$NR$^v$R$^w$ and —CH$_2$SO$_2$NR$^v$R$^w$, in which R$^v$ and R$^w$ independently represent hydrogen, C$_{1-6}$ alkyl, aryl or aryl(C$_{1-6}$)alkyl.

The term "halogen" as used herein includes fluorine, chlorine, bromine and iodine, especially fluorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Suitably, one of X and Y represents nitrogen, and the other represents CH.

In one specific embodiment, X represents nitrogen and Y represents CH.

In another specific embodiment, X represents CH and Y represents nitrogen.

Particular values of R$^1$ include 4-methylthiazol-2-yl and 4-hydroxymethylthiazol-2-yl. A preferred value of R$^1$ is 4-methylthiazol-2-yl.

Suitable values for the substituent R$^2$ include hydrogen, halogen, aryl, aryl(C$_{2-6}$)alkenyl, aryl(C$_{2-6}$)alkynyl, heteroaryl, aryloxy, aryl(C$_{1-6}$)alkoxy and heteroaryl(C$_{1-6}$) alkoxy, any of which groups may be optionally substituted by one or more substituents. Typical values of R$^2$ include hydrogen, halogen, aryl, aryl(C$_{2-6}$)alkenyl, aryl(C$_{2-6}$) alkynyl, heteroaryl, aryloxy and aryl(C$_{1-6}$)alkoxy, any of which groups may be optionally substituted by one or more substituents.

Representative values of R$^2$ include hydrogen, chloro, bromo, phenyl, phenylethenyl, phenylethynyl, pyridinyl, benzofuryl, thienyl, phenoxy, benzyloxy and pyridinylmetboxy, any of which groups may be optionally substituted by one or more substituents.

Typically, the group R$^2$ may be unsubstituted, or substituted by one or two substituents. Typical substituents on the group R$^2$ include halogen, C$_{1-6}$ hydroxyalkyl, C$_{1-6}$ alkoxy, C$_{1-3}$ alkylenedioxy, formyl and C$_{1-6}$ alkylthio.

Particular values of R$^2$ include hydrogen, chloro, bromo, phenyl, fluorophenyl, chlorophenyl, dichlorophenyl, hydroxymethyl-phenyl, methoxyphenyl, dimethoxyphenyl, (fluoro)(methoxy)phenyl, (chloro)(fluoro)phenyl, (chloro) (methoxy)phenyl, methylenedioxyphenyl, formylphenyl, methylthio-phenyl, phenylethenyl, phenylethynyl, pyridinyl, benzofuryl, thienyl, phenoxy, benzyloxy, fluorobenzyloxy, bromo-benzyloxy and pyridinylmethoxy.

Suitable values for the substituent R$^3$ include hydrogen, halogen, cyano, nitro, trifluoromethyl, amino, C$_{1-6}$ alkylamino. di(C$_{-6}$)alkylamino, C$_{1-6}$ alkyl, C$_{1-6}$ alkoxy, aryl (C$_{1-6}$)alkoxy, C$_{2-6}$ alkylcarbonyl and C$_{1-6}$ alkylsulphonyl. Particular values of R$^3$ include hydrogen and halogen, especially hydrogen or chloro, and typically hydrogen.

A particular sub-class of compounds according to the invention is represented by the compounds of formula Il, and salts and prodrugs thereof:

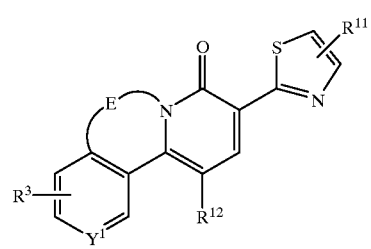

wherein
E is as defined with reference to formula I above;
Y$^1$ represents CH or nitrogen;
R$^{11}$ represents methyl or hydroxymethyl;
R$^{12}$ represents hydrogen, halogen, aryl, aryl(C$_{2-6}$)alkenyl, aryl(C$_{2-6}$)alkynyl, heteroaryl, aryloxy, aryl(C$_{1-6}$)alkoxy or heteroaryl(C$_{1-6}$)alkoxy, any of which groups may be optionally substituted by one or more substituents; and
R$^{13}$ represents hydrogen, halogen, cyano, nitro. trifluoromethyl, amino, C$_{1-6}$ alkylamino, di(C$_{1-6}$) alkylamino, C$_{1-6}$ alkyl, C$_{1-6}$ alkoxy, aryl(C$_{1-6}$)alkoxy, C$_{2-6}$ alkylcarbonyl or C$_{1-6}$ alkylsulphonyl.

The present invention also provides a compound of formula II as defined above, or a salt or prodrug thereof, wherein R$^{12}$ represents hydrogen, halogen, aryl, aryl(C$_{2-6}$) alkenyl, aryl(C$_{2-6}$)alkynyl, heteroaryl, aryloxy or aryl(C$_{1-6}$) alkoxy, any of which groups may be optionally substituted by one or more substituents; and E, Y$^1$, R$^{11}$ and R$^{13}$ are as defined above.

A particular value of R$^{11}$ is methyl, preferably in the 4-positioni of the thiazole ring.

Typically, the group R$^{12}$ may be unsubstituted, or substituted by one or two substituents.

Examples of suitable substituents on the moiety R$^{12}$ include halogen, C$_{1-6}$ hydroxyalkyl, C$_{1-6}$ alkoxy, C$_{1-3}$ alkylenedioxy, formyl and C$_{1-6}$ alkylthio. Typical substituents include fluoro, chloro, hydroxymethyl, methoxy, methylenedioxy, formyl and methylthio.

Particular values of R$^{12}$ include hydrogen, phenyl, fluorophenyl, chlorophenyl, dichlorophenyl, hydroxymethyl-phenyl, methoxyphenyl, dimethoxyphenyl, (fluoro)(methoxy)phenyl, (chloro)(fluoro)phenyl, (chloro) (methoxy)phenyl (especially 3-chloro-4-methoxyphenyl), methylenedioxyphenyl, formylphenyl, methylthio-phenyl, phenylethenyl, phenylethynyl, pyridinyl, benzofuryl, thienyl, phenoxy, benzyloxy, fluorobenzyloxy, bromobenzyloxy and pyridinylmethoxy.

Particular values of R$^{13}$ include hydrogen and halogen, especially hydrogen or chloro. A typical value of R$^{13}$ is hydrogen.

Specific compounds within the scope of the present invention include:
11-benzyloxy-9-(4-methylthiazol-2-yl)-6,7-dihydro-5H-2, 7a-diazadibenzo[α,c]cyclohepten-8-one;
11-(4-methoxyphenyl)-9-(4-methylthiazol-2-yl)-6,7-dihydro-5H-2,7a-diazadibenzo[α,c]cyclohepten-8-one;
11-(3-chloro-4-methoxyphenyl)-9-(4-methylthiazol-2-yl)-6, 7-dihydro-5H-2,7a-diazadibenzo[α,c]cyclohepten-8-one;
11-(4-fluorophenyl)-9-(4-methylthiazol-2-yl)-6,7-dihydro-5H-2,7a-diazadibenizo[α,c] cyclohepten-8-one;
11-(4-hydroxymethylphenyl)-9-(4-methylthiazol-2-yl)-6,7-dihydro-5H-2,7a-diazadibenzo[α,c]cyclohepten-8-one;
4-[9-(4-methylthiazol-2-yl)-8-oxo-6,7-dihydro-5H-2,7a-diazadibenzo[α,c]clcyclohepten-11-yl]benzaldehyde;
11-(2-methoxyphenyl)-9-(4-methylthiazol-2-yl)-6,7-dihydro-5H-2,7a-diazadibenzo[α,c]cyclohepten-8-one;

11-(3-methoxyphenyl)-9-(4-methylthiazol-2-yl)-6,7-dihydro-5H-2,7a-diazadibenzo[α,c]cyclohepten-8-one;
9-(4-methylthiazol-2-yl)-11-phenylethynyl-6,7-dihydro-5H-2,7a-diazadibenzo[α,c]cyclohepten-8-one;
9-(4-methylthiazol-2-yl)- 11-styryl-6,7-dihydro-5H-2,7a-diazadibenzo[α,c]cyclohepten-8-one;
9-(4-methylthiazol-2-yl)-6,7-dihydro-5H-2,7a-diazadibenzo[α,c]cyclohepten-8-one;
11-(3,4-methylenedioxyphenyl)-9-(4-methylthiazol-2-yl)-6,7-dihydro-5H-2,7a-diazadibenzo[α,c]cyclohepten-8-one;
11-(5-fluoro-2-methoxyphenyl)-9-(4-methylthiazol-2-yl)-6,7-dihydro-5H-2,7a-diazadibenzo[α,c]cyclohepten-8-one;
11-(4-methylsulfenylphenyl)-9-(4-methylthiazol-2-yl)-6,7-dihydro-5H-2,7a-diazadibenzo[α,c]cyclohepten-8-one;
9-(4-methylthiazol-2-yl)-11-phenyl-6,7-dihydro-5H-2,7a-diazadibenzo[α,c]cyclohepten-8-one;
11-(2,5-dimethoxyphenyl)-9-(4-methylthiazol-2-yl)-6,7-dihydro-5H-2,7a-diazadibenzo[α,c]cyclohepten-8-one;
9-(4-methylthiazol-2-yl)-11-(thien-3-yl)-6,7-dihydro-5H-2,7a-diazadibenzo[α,c]cyclohepten-8-one;
11-(3,5-dichlorophenyl)-9-(4-methylthiazol-2-yl)-6,7-dihydro-5H-2,7a-diazadibenzo[α,c]cyclohepten-8-one;
9-(4-methylthiazol-2-yl)-11-(thien-2-yl)-6,7-dihydro-5H-2,7a-diazadibenzo[α,c]cyclohepten-8-one;
11-(2,4-dimethoxyphenyl)-9-(4-methylthiazol-2-yl)-6,7-dihydro-5H-2,7a-diazadibenzo[α,c]cyclohepten-8-one;
11-(benzofuran-2-yl)-9-(4-methylthiazol-2-yl)-6,7-dihydro-5H-2,7a-diazadibenzo[α,c]cyclohepten-8-one;
11-(4-fluoro-2-methoxyphenyl)-9-(4-methylthiazol-2-yl)-6,7-dihydro-5H-2,7a-diazadibenzo[α,c]cyclohepten-8-one;
11-benzyloxy-9-(4-methylthiazol-2-yl)-6,7-dihydro-5H-3,7a-diazadibenzo[α,c]cyclohepten-8-one;
11-benzyloxy-2-hydroxy-9-(4-methylthiazol-2-yl)-6,7-dihydro-5H-2,7a-diazadibenzo[α,c]cyclohepten-8-one;
11-benzyloxy-9-(4-hydroxymethylthiazol-2-yl)-6,7-dihydro-5H-2,7a-diazadibenzo[α,c]cyclohepten-8-one;
1-benzyloxy-3-(4-methylthiazol-2-yl)-7,8-dihydro-6H-benzo[c]pyrido[1,2-α]azepin-4-one;
1-(4-methoxyphenyl)-3-(4-methylthiazol-2-yl)-7,8-dihydro-6H-benzo[c]pyrido[1,2-α]azepin-4-one;
10-benzyloxy-8-(4-methylthiazol-2-yl)-5H-pyrido[3,4-α]indolizin-7-one;
1-benzyloxy-3-(4-methylthiazol-2-yl)-6H-pyrido[2,1-α]isoindol-4-one;
1-benzyloxy-3-(4-methylthiazol-2-yl)-6,7-dihydropyrido[2,1-α]isoquinolin-4-one;
5-benzyloxy-7-(4-methylthiazol-2-yl)-9,10-dihydro-3,8a-diazaphenanthren-8-one;
5-(4-methoxyphenyl)-7-(4-methylthiazol-2-yl)-9,10-dihydro-3,8a-diazaphenanthren-8-one;
11-(2-bromobenzyloxy)-9-(4-methylthiazol-2-yl)-6,7-dibydro-5H-2,7a-diazadibenzo[α,c]cyclohepten-8-one;
11-(4-fluorobenzyloxy)-9-(4-methylthiazol-2-yl)-6,7-dihydro-5H-2,7a-diazadibenzo[α,c]cyclohepten-8-one;
9-(4-methylthiazol-2-yl)-11-phenoxy-6,7-dihydro-5H-2,7a-diazadibenzo[α,c]cyclohepten-8-one;
11-(2,4-dichlorophenyl)-9-(4-methylthiazol-2-yl)-6,7-dihydro-5H-2,7a-diazadibenzo[α,c]cyclohepten-8-one;
11-(3-chloro-4-fluorophenyl)-9-(4-methylthiazol-2-yl)-6,7-dihydro-5H-2,7a-diazadibenzo[α,c]cyclohepten-8-one;
11-(2-chlorophenyl)-9-(4-methylthiazol-2-yl)-6,7-dihydro-5H-2,7a-diazadibenzo[α,c]cyclohepten-8-one;
9-(4-methylthiazol-2-yl)-11-(pyridin-3-ylmethoxy)-6,7-dihydro-5H-2,7a-diazadibenzo[α, c]cyclohepten-8-one;
and salts and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof.

The binding affinity ($K_i$) of the compounds according to the present invention for the α3 subunit of the human $GABA_A$ receptor is conveniently as measured in the assay described hereinbelow. The α3 subunit binding affinity ($K_i$) of the compounds of the invention is ideally 10 nM or less, preferably 2 nM or less, and more preferably 1 nM or less.

The compounds according to the present invention will ideally elicit at least a 40%, preferably at least a 50%, and more preferably at least a 60%, potentiation of the GABA $EC_{20}$ response in stably transfected recombinant cell lines expressing the α3 subunit of the human $GABA_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the al subunit of the human $GABA_A$ receptor.

The potentiation of the GABA $EC_{20}$ response in stably transfected cell lines expressing the α3 and α1 subunits of the human $GABA_A$ receptor can conveniently be measured by procedures analogous to the protocol described in Wafford et al., *Mol. Pharinacol.*, 1996, 50, 670–678. The procedure will suitably be carried out utilising cultures of stably transfected eukaryotic cells, typically of stably transfected mouse Ltk fibroblast cells.

The compounds according to the present invention exhibit anxiolytic activity, as demonstrated by a positive response in the elevated plus maze and conditioned suppression of drinking tests (cf. Dawson et al., *Psychopharmacology*, 1995, 121, 109–117). Moreover, the compounds of the invention are substantially non-sedating, as confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate. dicalcium phosphate or gum-s, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidolne or gelatin.

In the treatment of anxiety, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises cyclising a compound of formula III:

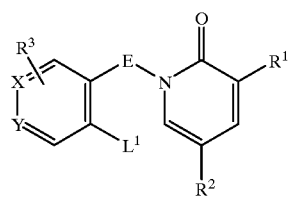

(III)

wherein E, X, Y, $R^1$, $R^2$ and $R^3$ are as defined above, and $L^1$ represents a readily displaceable group.

The readily displaceable group $L^1$ is suitably a halogen atom, e.g. bromo, in which case the cyclisation is conveniently carried out by treating the compound of formula III with tributyltin hydride in the presence of a radical initiator such as 1,1'-azobisisobutyronitrile (AIBN), typically in an inert solvent such as benzene.

The intermediates of formula III may suitably be prepared by reacting a compound of formula IV with a compound of formula V:

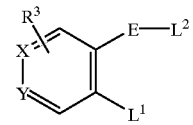

(IV)

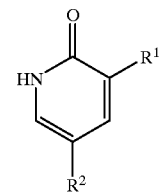

(V)

wherein E, X, Y, $R^1$, $R^2$, R3 and $L^1$ are as defined above, and $L^2$ represents a readily displaceable group.

The readily displaceable group $L^2$ may suitably be a halogen atom, e.g. bromo, in which case the reaction between compounds IV and V is conveniently effected by treatment with sodium hydride in the presence of lithium bromide, in a solvent system which may typically be a mixture of 1,2-dimethoxyethane and N,N-dimethylformamide. Alternatively, the readily displaceable group $L^2$ may be hydroxy, in which case the reaction between compounds IV and V is conveniently effected by treatment with triphenylphosphine in the presence of diethyl azodicarboxylate (DEAD), typically in an inert solvent such as dichloromethane.

Where they are not commercially available, the starting materials of formula IV and V may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula I initially obtained wherein $R^2$ represents benzyloxy may be converted into the corresponding compound of formula I wherein $R^2$ represents aryl, aryl($C_{2-6}$)alkenyl or aryl($C_{2-6}$)alkynyl by a stepwise process which comprises debenzylation using boron tribromide in dichloromethane; treatment of the resulting hydroxy compound with trifluoromethanesulphonic anhydride in the presence of pyridine to afford the corresponding triflate derivative; and reaction of the latter compound with the appropriate aryl or aryl($C_{2-6}$)alkenyl boronic acid in the presence of tetrakis(triphenylphosphine)palladium(0) and sodium carbonate, or with the appropriate aryl($C_{2-6}$)alkyne in the presence of bis(triphenylphosphine)palladium(II) chloride, triethylamine and N,N-dimethylformamide, to obtain the desired product of formula I. Moreover, compound of formula I initially obtained wherein $R^2$ represents enzyloxy may be converted into the corresponding compound of formula I wherein $R^2$ represents heteroaryl($C_{1-6}$) alkyl by debenzylation as described above followed by treatment of the resulting hydroxy compound with an alkylating agent, for example a heteroaryl($C_{1-6}$)alkyl halide such as 3-picolyl chloride, typically in the presence of sodium hydride in a solvent such as N,N-dimethylformamide.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific or enantioselective synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid andlor (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human $GABA_A$ receptors containing the α2 or α3 subunit stably expressed in Ltk cells.

Reagents

Phosphate buffered saline (PBS).

Assay buffer: 10 mM $KH_2PO_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells) in assay buffer.

Flunitrazepam 100 μM in assay buffer.

C Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM).

50 μl of buffer or solvent carrier (e.g. 10% DMSO) if compounds are issolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]-flumazenil from the α2 and/or α3 subunit of the human $GABA_A$ receptor of 100 nM or less.

EXAMPLE 1

11-Benzyloxy-9-(4-methylthiazol-2-yl)-6,7-dihydro-5H-2,7a-diazadibenzo[α,c]cyclohepten-8-one Step 1: 2-Benzyloxy-3-(N,N-dimethylamino)propenal Prepared by a modification of the literature procedure reported in *Croat. Chim. Acta*, 1966, 235. Phosphorus pentachloride (0.13 mol) was added to benzyloxyacetaldehyde diethyl acetal (0.13 mol) at 20–30° C. The reaction mixture was heated at 60° C. for 75 min and then cooled to 0° C. The reaction mixture was treated with DMF (0.39 mol) and stirred at room temperature for four days. The reaction mixture was diluted with 1.0N HCl(aq) (200 ml) and ether (200 ml). The ether layer was discarded and the aqueous layer was basified with 8N NaOH(aq). The aqueous layer was extracted with ethyl acetate and ether and the combined organic extracts were dried (MgSO4), filtered and evaporated in vacuo. The resulting black oil was purified by column chromatography to give the product as a brown solid (0.06 mol, 43%). $\delta_H$ (250 MHz; CDCl$_3$) 8.62 (1H, s), 7.44-7.26 (5H, m), 6.18 (1H, s), 4.96 (2H, s), 3.04 (6H, s).

Step 2: 5-Benzyloxy-3-(4-methylthiazol-2-yl)-1H-pyridin-2-one 2-(4-Methylthiazol-2-yl)acetamide (0.016 mol), 2-benzyloxy-3-(N,N-dimethylamino)propenal (0.017 mol), sodium hydride (0.032 mol), methanol (1.3 ml) and DMF (100 ml) were heated at 70° C. for 4 h. The reaction was cooled, acidified with 5.0N HCl(aq), and poured into water. The resulting precipitate was collected by filtration and dried to give the product as a brown solid (11.7 mmol, 73%). $\delta_H$ (360 MHz; CDCl$_3$) 9.38 (1H, s), 7.47-7.34 (7H, m), 7.09 (1H, s), 5.21 (2H, s), 2.69 (3H, s).

Step 3: 5-Benzyloxy-1-[3-(3-bromopyridin-4-yl)propyl]-3-(4-methylthiazol-2-yl)-1H-pyridin-2-one Prepared by a modification of the procedure reported in *Tetrahedron Lett.*, 1995, 8917. 5-Benzyloxy-3-(4-methylthiazol-2-yl)-1H-pyridin-2-one (3.3 mmol) was dissolved in DMF (5 ml) and DME (20 ml). The reaction mixture was cooled to 0° C. and treated with sodium hydride (3.5 mmol). After 10 min, the reaction mixture was treated with lithium bromide (6.6 mmol) and stirred for 15 min at room temperature. The reaction mixture was treated with a solution of 4-(3-bromopropyl)-3-bromopyridine (5.0 mmol) in DME (5 ml) and then it was heated at 75° C. for 60 h. The reaction mixture was cooled, acidified, and washed with ethyl acetate. The aqueous layer was basified and extracted with ethyl acetate. The organic extracts were dried (MgSO$_4$), filtered, and evaporated in vacuo. Purification by column chromatography gave the product as a yellow foam (2.74 mmol, 82%). $\delta_H$ (250 MHz; CDCl$_3$) 8.65 (1H, s), 8.60 (1H, brd), 8.41 (1H, d, J=7.1), 7.40-7.33 (5H, m), 7.16 (1H, d, J=7.3), 7.03 (1H, s), 7.00 (1H, d, J=4.6), 5.02 (2H, s), 4.13 (2H, t, J=10.4), 2.79-2.72 (2H, m), 2.53 (3H, s), 2.17-2.04 (2H, m).

Step 4: 11-Benzyloxy-9-(4-methylthiazol-2-yl)-6,7-dihydro-5H-2,7a-diazadibenzo[α,c]cyclohepten-8-one 5-Benzyloxy-1-[3-(3-bromopyridin-4-yl)propyl]-3-(4-methylthiazol-2-yl)-1H-pyridin-2-one (2.0 mmol) was dissolved in benzene, treated with tributyltin hydride (4.0 mmol) and AIBN (2.0 mmol) and refluxed for 16 h. The reaction mixture was evaporated in vacuo, and the residue was partitioned between 2.0N HCl (aq) and ethyl acetate. The aqueous layer was washed with ethyl acetate, then basified and extracted with ethyl acetate. The ethyl acetate extracts were combined, dried (MgSO4), filtered and evaporated in vacuo to give a crude oil. Purification by column chromatography gave the ring-closed product (total yield approximately 1.0 mmol, 50%). $\delta_H$ (360 MHz; CDCl$_3$) 8.83 (1H, s), 8.81 (1H, s), 8.60 (1H, d, J=6.0), 7.37-6.99 (7H, m), 5.17-5.09 (2H, m), 4.85 (1H, d, J=11.6), 3.07-2.99 (lH, m), 2.58-2.39 (5H, m), 2.17-2.08 (1H, m), 1.97-1.87 (lH, m).

EXAMPLE 2

11-(4-Methoxyohenyl)-9-(4-methylthiazol-2-yl)-6,7-dihydro-5H-2,7a-diazadibenzo[α,c]cycloheoten-8-one Step 1: 11-Hydroxy-9-(4-methylthiazol-2-yl)-6,7-dihydro-5H-2,7a-diazadibenzo[α,c]cycloheoten-8-one 11-Benzyloxy-9-(4-methylthiazol-2-yl)-6,7-dihydro-5H-2,7a-diazadibenzo[α,c]cyclohepten-8-one was dissolved in dichloromethane and cooled to 0° C. A solution of boron tribromide in dichloromethane (2.0 mmol) was added slowly and the reaction mixture was allowed to warm to room temperature. The reaction mixture was treated with methanol, ether and 4.0N NaOH(aq). The aqueous layer was washed with ether, then carefully neutralized with HCl(aq). The aqueous mixture was extracted with ethyl acetate. The ethyl acetate extracts were combined, dried (MgSO$_4$), filtered and evaporated to give the desired phenol as a yellow powder (yield approximately 0.9 mmol, 90%). $\delta_H$ (360 MHz; CDCl$_3$) 8.91 (1H, s), 8.58 (1H, d), 8.30 (1H, s), 7.27 (1H, s), 7.07 (1H, s), 5.15 (1H, dd, J=13.2, 5.5), 3.18-3.09 (1H, m), 2.80-2.74 (1H, m), 2.68-2.50 (5H, m), 2.28 (1H, s), 2.05-2.00 (1H, m).

Step 2: 9-(4-Methylthiazol-2-yl)-11-trifluoromethanesulfonyloxy-6,7-dihydro-5H-2,7a-diazadibenzo[α,c]cyclohepten-8-one The foregoing phenol (1.7 mmol) was dissolved in dichloromethane (30 ml) and pyridine (2.6 mmol) and cooled to −78° C. The reaction mixture was treated with triflic anhydride (2.2 mmol) and allowed to warm to room temperature. The reaction mixture was diluted with dichloromethane, washed with sodium carbonate solution, and brine, dried (MgSO$_4$), filtered and evaporated iii vacuo. Purification by flash column chromatography gave the desired triflate as a yellow powder (yield approximately 1.2 mmol, 73%). $\delta_H$ (360 MHz; CDCl$_3$) 8.77 (1H, s), 8.76 (1H, d), 8.62 (1H, s), 7.33 (1H, d, J=4.9), 7.11 (1H, s), 5.23 (1H, dd, J=5.4, 13.4), 3.17-3.10 (1H, m), 2.88-2.82 (1H, m), 2.70-2.55 (5H, m), 2.10-2.04 (1H, m).

Step 3: 11-(4-Methoxyphenyl)-9-(4-methylthiazol-2-yl)-6,7-dihydro-5H-2,7a-diazadibenzo[α, c]cycloheoten-8-one The foregoing triflate (0.11 mmol) and 4-methoxyphenylboronic acid (0.22 mmol) were dissolved in DME (5 ml) and 2.0N Na$_2$CO$_3$(aq). Freshly prepared Pd(PPh$_3$)$_4$ (catalytic quantity) was added and the reaction mixture was heated at 100° C. under a nitrogen atmosphere for 2 h. The reaction mixture was cooled and diluted with ethyl acetate and 2.0N HCl(aq). The aqueous layer was separated and washed with ethyl acetate. The aqueous layer was basified and extracted with ethyl acetate. The combined ethyl acetate extracts were dried (MgSO$_4$), filtered and evaporated i71 vacuo to give a crude solid. Purification by flash column chromatography or trituration with ethyl acetate gave the product. $\delta_H$ (360 MHz; CDCl$_3$) 8.75 (1H, s), 8.47 (1H, d, J=5.0), 8.05 (1H, s), 7.24 (1H, d, J=5.0), 7.05 (1H, s), 6.92 (2H, d, J=8.6), 6.74 (2H, d, J=8.6), 5.30 (1H, dd, J=5.5, 13.5), 3.76 (3H, s), 3.12-3.06 (1H, m), 2.86-2.77 (2H, m), 2.66-2.52 (4H, m), 2.08-2.02 (1H, m).

EXAMPLE 3

11-(3-Chloro-4-methoxyrphenyl)-9-(4-methylthiazol-2-yl)-6,7-dihydro-5H-2,7a-diazadibenzo[α,c]cyclohepten-8-one $\delta_H$ (360 MHz; CDCl$_3$) 8.75 (1H, s), 8.47 (1H, d, J=5.0), 8.07 (1H, s), 7.24 (1H, d, J=5.0), 7.05 (2H, 2 x s), 6.84-6.71 (21, m), 5.30 (1H, dd, J=5.5, 13.5), 3.86 (3H, s), 3.15-3.06 (1H, m), 2.91-2.71 (2H, m), 2.60-2.52 (4H, m), 2.08-2.02 (1H, m).

EXAMPLE 4

11-(4-Fluorophenyl)-9-(4-methylthiazol-2-yl)-6,7-dihydro-5H-2,7a-diazadibenzo[α,c]cyclohepten-8-one $\delta_H$ (360 MHz; CDCl$_3$) 8.75 (1H, s), 8.47 (1H, d, J=5.0), 8.02 (1H, s), 7.24 (1H, d, J=5.0), 7.06 (1H, s), 6.98-6.89 (4H, m), 5.31 (1H, dd, J=5.5, 13.5), 3.15-3.06 (1H, m), 2.91-2.52 (6H, mi), 2.08-2.02 (1H, m).

EXAMPLE 5

11-(4-Hydroxymethylphenyl)-9-(4-methylthiazol-2-yl)-6,7-dihydro-5H-2,7a-diazadibenzo[α,c]cyclohepten-8-one $\delta_H$ (360 MHz; CDCl$_3$) 8.75 (1H, s), 8.46 (1H, d, J=5.0), 8.02 (1H, s), 7.26-7.20 (3H, m), 7.05 (1H, s), 6.99 (21, d, J=8.0), 5.31 (1H, dd, J=5.5, 13.5), 4.64 (2H, s), 3.15-3.07 (1H, m), 2.92-2.75 (211, m), 2.61-2.52 (4H, m), 2.06-2.02 (1H, m), 1.8 (1H, br s).

EXAMPLE 6

4-[9-(4-Methylthiazol-2-yl)-8-oxo-6,7-dihydro-5H-2,7a-diazadibenzo[E,c]cyclohepten-11-yl]benzaldebyde $\delta_H$ (360 MHz; CDCl$_3$) 9.96 (1H, s), 8.68 (1H, s), 8.51 (1H, d, J=5.0), 8.00 (1H, s), 7.75 (2H, d, J=8.4), 7.28 (1H, d, J=4.9), 7.19 (2H, d, J=8.4), 7.07 (1H, s), 5.31 (1I1, dd, J=5.5, 13.5), 3.17-3.09 (1H, m), 2.95-2.77 (2H, m), 2.67-2.53 (1H, m), 2.53 (3H, s), 2.06-2.02 (1H, m).

EXAMPLE 7

11-(2-Methoxyphenyl)-9-(4-methylthiazol-2-yl)-6,7-dihydro-5H-2,7a-diazadibenzo[α,c]cyclohepten-8-one $\delta_H$(360 MHz; d$_6$-DMSO) 8.41-8.39 (2H, m), 7.95 (1H, s), 7.36 (2H, d, J=4.8), 7.29-7.26 (2H, m), 7.10-6.90 (2H, br m), 5.13-5.08 (1H, m), 3.08-2.88 (5H, m), 2.70-2.35 (5H, m), 2.05-2.00 (1H, m).

EXAMPLE 8

11-(3-Methoxyplhenyl)-9-(4-methylthiazol-2-yl)-6,7-dihydro-5H-2,7 a-diazadibenzo[α,c]cycloheoten-8-one $\delta_H$ (360 MHz; CDCl$_3$) 8.68 (1H, s), 8.48 (1H, d, J=5.0), 8.08 (1H, s), 7.23 (1H, d, J=4.9), 7.11 (1H, t, J=7.9), 7.05 (1H, s), 6.75 (1H, dd, J=7.7, 2.5), 6.58 (1H, s), 6.54 (1H, d, J=7.6), 5.31 (1H, dd, J=5.5, 13.5), 3.70 (3H, s), 3.16-3.07 (1H, m), 2.90-2.73 (2H, m), 2.66-2.52 (4H, m), 2.06-2.02 (1H, m).

EXAMPLE 9

9-(4-Methylthiazol-2-yl)-11-styryl-6,7-dihydro-5H-2,7a-diazadibenzo[α,c]cyclohepten-8-one $\delta_H$ (360 MHz; CDCl$_3$) 8.70 (1H, d, J=5.0), 8.62 (1H, d, J=5.0), 7.37-7.07 (9H, m), 6.78 (1H, d, J=16.1), 5.26 (1H, dd, J=5.5, 13.5), 3.11-3.03 (1H, m), 2.85-2.79 (1H, m), 2.69-2.52 (5H, m), 2.05-2.00 (1H, m).

EXAMPLE 10

9-(4-Methylthiazol-2-yl)-6,7-dihydro-5H-2,7a-diazadibenzo[α,c]cyclohepten-8-one $\delta_H$ (360 MHz; CDCl$_3$) 8.78-8.60 (3H, m), 7.25 (1H, d, J=4.7), 7.03 (1H, s), 6.54 (1H, d, J=7.4), 5.24 (1H, br s), 3.19 (1H, br s), 2.90-2.40 (6H, br s), 2.10-2.00 (1H, br s).

EXAMPLE 11

11-(3,4-Methylenedioxyphenyl)-9-(4-methylthiazol-2-yl)-6,7-dihydro-5H-2,7a-diazadibenzo[α,c]cyclohepten-8-one δ$_H$ (360 MHz; CDCl$_3$) 8.72 (1H, s), 8.48 (1H, d, J=5.0), 8.11 (1H, s), 7.24 (1H, d, J=4.9), 7.05 (1H, s), 6.66 (1H, d, J=8.2), 6.47 (1H, s), 6.45 (1H, s), 5.93 (2H, s), 5.30 (1H, dd, J=5.4, 13.6), 3.08 (1H, m), 2.90-2.84 (1H, m), 2.80-2.70 (1H, m), 2.59-2.50 (4H, m), 2.00-1.88 (1H, m).

EXAMPLE 12

11-(5-Fluoro-2-methoxyphenyl)-9-(4-methylthiazol-2-yl)-6,7-dihydro-5H-2,7a-diazadibenzo[α,c]cyclohepten-8-one $^1$H NMR 250 MHz (CDCl$_3$) δ 2.07 (1H, m), 2.52 (3H, s), 2.50–2.70 (1H, m), 2.81–2.85 (2H, m), 3.13 (3H, bs), 3.90 (1H, bs), 5.30–5.33 (1H, m), 6.49 (1H, m), 6.89–6.92 (1H, m), 6.90 (1H, s), 7.20–7.26 (1H, m), 7.47 (1H, m), 8.08 (1H, m), 8.43 (1H, m), 8.62 (1H, s). Mass Spec ES$^+$ (M+1)=434.

EXAMPLE 13

11-(4-Methylsulfenylphenyl)-9-(4-methylthiazol-2-yl)-6,7-dihydro-5H-2,7a-diazadibenzo[α,c]cyclohepten-8-one $^1$H NMR 360 MHz (CDCl$_3$) δ 2.06 (1H, m), 2.44 (3H, s), 2.52 (3H, s), 2.56–2.60 (1H, m), 2.73–2.90 (2H, m), 3.09 (1H, dt, J=5.0, 13.4 Hz), 5.31 (1H, dd, J=5.43, 13.4), 6.91 (2H, d, J=8.3Hz), 7.08 (3H, m), 7.25 (1H, m), 8.06 (1H, s), 8.49 (1H, d, J=5.0 Hz), 8.72 (1H, s). Mass spec ES$^+$ (M+1)=432.

EXAMPLE 14

9-(4-Methylthiazol-2-yl)-11-phenyl-6,7-dihydro-5H-2,7a-diazadibenzo[α,c]cyclohepten-8-one $^1$H NMR 360 MHz (CDCl$_3$) δ 2.04 (1H, m), 2.52 (3H, s), 2.57–2.61 (1H, m), 2.74–2.91 (2H, m), 3.07–3.15 (1H, dt, J=5.0, 13.4 Hz), 5.32 (1H, dd, J=5.4, 13.4 Hz), 7.00–7.05 (3H, m), 7.21–7.26 (4H, m), 8.03 (1H, s), 8.47 (1H, d, J=5.0 Hz), 8.78 (1H, s). Mass spec ES$^+$ (M+1)=386.

EXAMPLE 15

11-(2,5-Dimethoxyphenyl)-9-(4-methylthiazol-2-yl)-6,7-dihvdro-5H-2,7a-diazadibenzo[α,c]cyclohepten-8-one Mass spec ES$^+$ (M+1)=446.

EXAMPLE 16

9-(4-Methylthiazol-2-yl)-11-(thien-3-yl)-6,7-dihydro-5H-2,7a-diazadibenzo[α,c]cyclohepten-8-one $^1$H NMR (CDCl$_3$, 360 MHz) δ 2.00–2.05 (1H, m), 2.53 (3H, s), 2.55–2.63 (1H, m), 2.73–2.89 (2H, m), 3.11 (1H, dt, J=5.0, 13.4 Hz), 5.30 (1H, dd, J=5.4, 13.4 Hz), 6.52 (1H, d, J=5.0 Hz), 7.04 (2H, s), 7.16 (1H, m), 7.25 (1H, m), 8.15 (1H, s), 8.48 (1H, d, J=5.0 Hz), 8.78 (1H, s). Mass spec ES$^+$ (M+1)=392.

EXAMPLE 17

11-(3,5-Dichlorophenyl)-9-(4-methylthiazol-2-yl)-6,7-dihvdro-5H-2,7a-diazadibenzo[α,c]cyclohepten-8-one Mass spec ES$^+$ (M+1)=454.

EXAMPLE 18

9-(4-Methylthiazol-2-yl)-11-(thien-2-yl)-6,7-dihydro-5H-2,7a-diazadibenzo[α,c]cyclohe-ten-8-one $^1$H NMR (CDCl$_3$, 360 MHz) δ 2.04 (1H, m), 2.53 (3H, s), 2.57 (1H, m), 2.70–2.89 (2H, m), 3.11 (1H, dt, J=5.0, 13.4 Hz), 5.30 (1H, dd, J=5.4, 13.4 Hz), 6.81 (1H, m?), 6.89 (1H, m), 7.06 (1H, s), 7.18 (1H, m), 7.26 (1H, m), 8.29 (1H, s), 8.48 (1H, d, J=5.0 Hz), 8.78 (1H, s). Mass spec ES$^+$ (M+1)=399.

EXAMPLE 19

11-(2 4-Dimethoxyphenyl)-9-(4-methylthiazol-2-yl)-6,7-dihydro-5H-2,7a-diazadibenzo[α,c]cycloheoten-8-one Mass spec ES$^+$ (M+1)=446.

EXAMPLE 20

11-(Benzofuran-2-yl)-9-(4-methylthiazol-2-yl)-6,7-dihydro-5H-2,7a-diazadibenzo[α,c]cyclohelten-8-one Mass spec ES$^+$ (M+1)=426.

EXAMPLE 21

11-(4-Fluoro-2-methoxyphenyl)-9-(4-methylthiazol-2-yl)-6,7-dihydro-5H-2,7a-diazadibenzo[α,c]cyclohepten-8-one $^1$H NMR (DMSO, 360 MHz) δ 1.99 (1H, m), 2.34 (1H, m), 2.42 (3H, s), 2.59 (1H, m), 2.91–3.03 (1H, m), 3.04–3.14 (3H, m), 3.92 (1H, s), 5.05 (1H, m), 6.62–6.65 (1H, m), 6.69–7.10 (1H, m), 7.34 (1H, s), 7.41–7.42 (1H, m), 7.59 (1H, m), 7.88–7.93 (1H, m), 8.37 (1l1, m), 8.44 (1H, m). Mass spec ES$^+$ (M+1)=434.

EXAMPLE 22

11-Benzyloxy-9-(4-methylthiazol-2-yl)-6,7-dihydro-5H-3,7a-diazadibenzo[αc,]cyclohepten-8-one δH (360 MHz; CDCl$_3$) 8.73 (1H, s), 8.59 (1H, d, J=5.0), 8.40 (1H, s), 7.51 (1H, d, J=5.0), 7.26-7.00 (6H, m), 5.15-5.06 (2H, m), 4.81 (1H, d, J=11.6), 3.05-2.97 (1H, m), 2.63-2.44 (5H, m), 2.10-1.87 (2H, m).

EXAMPLE 23

11-Benzyloxy-2-hvdroxy-9-(4-methylthiazol-2-yl)-6,7-dihydro-5H-2,7a-diazadibenzo[α,c]cyclohepten-8-one δH (500 MHz; DMSO) 8.64 (1H, s), 8.33 (1H, s), 8.24 (1H, d, J=6.7), 7.40-7.10 (7H, m), 5.17 (1H, d, J=11.7), 4.97 (1H, d, J=11.7), 4.91 (1H, m), 3.13 (1H, m), 2.68 (1H, m), 2.49 (3H, s), 2.20-1.90 (3H, m).

EXAMPLE 24

11-Benzyloxy-9-(4-hydroxymethylthiazol-2-yl)-6,7-dihydro-5H-2,7a-diazadibenzo[α,c]cyclohepten-8-one δH (500 MHz; DMSO) 8.74 (1H, s), 8.65 (1H, s), 8.59 (1H, d, J=4.6), 7.53-7.10 (7H, m), 5.11 (1H, d, J=11.5), 4.94 (1H, m), 4.89 (1H, d, J=11.5), 4.69 (2H, s), 3.02 (1H, m), 2.79 (1H, m), 2.26 (2H, m), 1.96 (1H, m).

EXAMPLE 25

1-Benzyloxy-3-(4-methylthiazol-2-yl)-7,8-dihydro-6H-benzo[c]pyrido[1,2-α]azepin-4-one δH (360 MHz; CDCl$_3$ 8.72 (1H, br s), 7.63 (1H, dd, J=1.3, 7.5), 7.39 (2H, m), 7.18 (4H, m), 7.01 (3H, m), 5.13 (1H, dd, J=5.7, 13.1), 4.97 (1H, d, J=11.4), 4.74 (1H, d, J=11.4), 3.09 (1H, dt, J=5.2, 13.1), 2.58 (1H, m), 2.56 (3H, m), 2.40 (1H, m), 2.21 (1H, m), 1.91 (1H, m).

EXAMPLE 26

1-(4-Methoxyphenyl)-3-(4-methylthiazol-2-yl)-7,8-dihydro-6H-benzo[c]pyrido[1,2-α]azepin-4-one δH (360 MHz; CDCl$_3$) 8.71 (1H, s), 7.26 (2H, m), 6.97 (2H, m), 6.92 (2H, d, J=8.7), 6.84 (1H, d, J=7.4), 6.71 (2H, d, J=8.7), 5.26 (1H, dd, J=5.5, 13.2), 3.76 (3H, s), 3.13 (1H, dt, J=5.0, 13.2), 2.82 (1H, m), 2.72 (1H, m), 2.51 (3H, m), 2.50 (1H, m), 1.99 (1H, m).

EXAMPLE 27

9-(4-Methylthiazol-2-yl)-11-phenylethynyl-6,7-dihydro-5H-2,7a-diazadibenzo[α,c]cyclohepten-8-one A solution of the triflate from Example 2, Step 2 (0.1 mmol), phenylacetylene (0.5 mmol), DMF (2.5 ml), triethylamine (1 ml) and bis(triphenylphosphine)palladium(II) chloride (10 mg) was heated in a sealed tube at 100° C. for 3h. The reaction mixture was cooled, poured into 2N HCl (aq) and washed with ethyl acetate. The aqueous layer was basified and extracted with ethyl acetate. The ethyl acetate extracts were washed with brine, dried, filtered and evaporated in vacuo. The crude solid was taken up in dichloromethane-ether and washed sequentially with water, pH 4 buffer solution, sodium bicarbonate solution and water. The organic phase was dried, filtered and evaporated to give the product as a solid, about 60% yield. $^\delta$H (360 MHz; CDCl$_3$) 9.17 (1H, s), 8.86 (1H, s), 8.68 (1H, d, J=5.0), 7.33-7.26 (5H, m), 7.07 (1H, s), 5.25 (1H, dd, J=5.5, 13.5), 3.16-3.07 (1H, m), 2.90-2.70 (7H, m), 2.06-2.02 (1H, m).

EXAMPLE 28

10-Benzyloxy-8-(4-methylthiazol-2-yl)-5H-pyrido[3,4-α]indolizin-7-one

Step 1: 5-Benzyloxy-1-(4-bromopyridin-3-ylmethyl)-3-(4-methylthiazol-2-yl)-1H-pyridin-2-one 5-Benzyloxy-3-(4-methylthiazol-2-yl)-1H-pyridin-2-one (1.0 mmol), 4-bromo-3-hydroxyniethylpyridine (1.0 mmol), triphenylphosphine (1.5 mmol), diethyl azodicarboxylate (1.5 mmol) and THF (10 ml) were mixed and stirred at room temperature for 0.5 h. The reaction mixture was acidified, and washed with ether. The aqueous layer was basified and extracted with ether. The ethereal extracts were dried (MgSO4), filtered, and evaporated in vacuo. Purification by column chromatography gave the desired product as a yellow foam (0.58 mmol, 58%).

Step 2: 10-Benzyloxy-8-(4-methylthiazol-2-yl)-5H-pyrido[3,4-α]indolizin-7-one

Prepared according to the procedure described in Example 1, Step 4. $^\delta$H (360 MHz; CDCl$_3$) 8.92 (1H, s), 8.89 (1H, br s), 8.70 (1H, d, J=5.0), 7.89 (1H, d, J=4.3), 7.53-7.40 (5H, m), 7.10 (1H, s), 5.35 (4H, 2 x s), 2.57 (3H, s).

EXAMPLE 29

1-Benzyloxy-3-(4-methylthiazol-2-yl)-6H-pyrido[2,1-α]isoindol-4-one $^\delta$H (360 MHz; CDCl$_3$) 8.80 (1H, s), 8.10 (1H, d, J=6.7), 7.62-7.40 (8H, m), 7.03 (1H, s), 5.30 (2H, s), 5.28 (2H, s), 2.55 (3H, s).

EXAMPLE 30

1-Benzyloxy-3-(4-methylthiazol-2-yl)-6,7-dihydropyrido[2,1-α]isoquinolin-4-one $^\delta$H (250 MHz; CDCl$_3$) 8.70 (1H, s), 8.42 (1H, d, J=6.8), 7.40-7.26 (8H, m), 7.04 (1H, s), 5.06 (2H, s), 4.42 (2H, m), 2.94 (2H. dd, J=6.5, 6.5), 2.56 (3H, s).

EXAMPLE 31

5-Benzyloxy-7-(4-methylthiazol-2-yl)-9,10-dihydro-3,8a-diazaphenanthren-8-one $^\delta$H (250 MHz; d$_4$-MeOH) 9.00 (1H, s), 8.47 (1H, s), 8.14 (1H, d, J=9.4), 7.48-7.45 (1H, d, J=9.4), 7.01 (1H, s), 6.82-6.73 (5H, m), 4.74 (2H, s), 3.89 (2H, t, J=9.0), 2.76-2.69 (2H, m), 2.04 (3H, s).

EXAMPLE 32

5-(4-Methoxyphenyl)-7-(4-methylthiazol-2-yl)-9,10-dihydro-3,8a-diazaphenanthren-8-one $^\delta$H (360 MHz; CDCl$_3$) 8.62 (1H, s), 8.40 (1H, d, J=4.9), 8.21 (1H, s), 7.22-7.16 (3H, m), 7.04 (1H, s), 6.91-6.88 (2H, m), 4.42 (2H, t, J=6.0), 3.88 (3H,), 3.05 (2, t, J=6.0), 2.51 (3H, s).

EXAMPLE 33

11-(2-Bromobenzyloxy)-9-(4-methylthiazol-2-yl)-6,7-dihydro-5H-2,7a-diazadibenzo[α,c]cyclohepten-8-one The product from Example 2, Step 1 (0.15 mmol) was dissolved im DMF (2 ml) and treated with sodium hydride (0.23 mmol). After 10 minutes at room temperature, the reaction mixture was treated with 2-bromobenzyl bromide (0.23 mmol) and stirred at room temperature for 1 h. The reaction mixture was diluted with ethyl acetate and water. The aqueous phase was extracted with ether. The combined organic extracts were dried (MgSO$_4$), filtered and evaporated in vacuo. Purification by column chromatography gave the desired product. $^\delta$H (360 MHz; CDCl$_3$) 8.83 (2H, s x 2), 8.58 (1H d, J=5.0), 7.40 (1H, d, J=7.6), 7.17-7.07 (5H, m), 5.20-5.15 (2H, m), 4.93 (1H, d, J=12.1), 3.09-3.00 (1H, m), 2.63-2.47 (5H, m), 2.34-2.25 (1H, m), 2.05-2.00 (1H, m).

EXAMPLE 34

11-(4-Fluorobenzyloxy)-9-(4-methylthiazol-2-yl)-6,7-dihydro-5H-2,7a-diazadibenzo[α,c]cyclohepten-8-one $^\delta$H (360 MHz; CDCl$_3$) 8.90 (2H, m), 8.58 (1H, d, J=5.0), 7.14 (1H, d, J=4.9), 7.07 (1H, s), 6.99-6.95 (2H, m), 6.85-6.80 (2H, m), 5.14 (1H, dd, J=5.8, 13.5), 5.05 (1H, d, J=11.6), 4.79 (1H, d, J=11.6), 3.03 (1H, m), 2.60-2.54 (4H, m), 2.49-2.44 (1H, m), 2.20-2.10 (1H, m), 2.00-1.88 (1H, m).

EXAMPLE 35

9-(4-Methylthiazol-2-yl)-11-phenoxy-6,7-dihydro-5H-2,7a-diazadibenzo[α,c]cyclohepten-8-one $^1$H NMR 250 MHz (CDCl$_3$) δ 2.05–2.08 (1H, m), 2.49 (3H, s), 2.59–2.66 (2H, m), 2.76–2.84 (1H, m), 3.13–3.23 (1H, m), 5.23–5.30 (1H, m), 6.84 (1H, s), 6.87 (1H, s), 6.98–7.06 (2H, m), 7.20–7.28 (3H, m), 8.58 (2H, s), 8.78 (1H, s), Mass spec ES$^+$ (M+1)=402.

EXAMPLE 36

11-(2,4-Dichlorophenyl)-9-(4-methylthiazol-2-yl)-6,7-dihydro-5H-2 7a-diazadibenzo[α,c]cycloheoten-8-one Mass spec ES$^+$ (M+1)=454, 456, 458.

EXAMPLE 37

11-(3-Chloro-4-fluorophenyl)-9-(4-methylthiazol-2-yl)-6,7-dihydro-5H-2,7a-diazadibenzo[α,c]cyclohe-ten-8-one Mass spec ES$^+$ (M+1)=438.

EXAMPLE38

11-(2-Chlorolhenyl)-9-(4-methylthiazol-2-yl)-6,7-dihydro-5H-2,7a-diazadibenzo[α,c]cyclohepten-8-one Mass spec ES$^+$ (M+1)=420, 422.

EXAMPLE 39

9-(4-Methylthiazol-2-yl)-11-(pyridin-3-ylmethoxy)-6,7-dihydro-5H-2,7a-diazadibenzo[α,c]cyclohepten-8-one 11-Hydroxy-9-(4-methylthiazol-2-yl)-6,7-dihydro-5H-2,7a-diazadibenzo[α,c]cyclohepten-8-one (Example 2, Step 1) (0.31 mmol) in DMF (3 ml) was treated with sodium hydride (0.37 mmol as a 60% w/w dispersion in mineral oil) and left for 5 minutes. 3-Picolyl chloride (0.46 mmol) was added and the reaction left to stir overnight. Diluted (DCM/H$_2$O). Organic layer washed (H$_2$O, brine), dried (MgSO$_4$) and evaporated in vacuo. Purified by flash silica chromatography to afford the product as a foam. Mass spec ES$^+$ (M+1)=417.

What is claimed is:

1. A compound of formula 1, or a salt thereof:

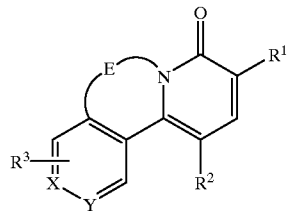

wherein

E represents —(CH$_2$)$_n$—;

n is 3;

one of X and Y represents CH, nitrogen or N$^+$—O$^-$, and the other represent CH;

R$^1$ represents methoxycarbonyl, ethoxycarbonyl, methylthiazolyl or hydroxymethylthiazolyl;

R$^2$ and R$^3$ independently represent hydrogen, C$_{1-6}$alkyl, C$_{2-6}$alkenyl, C$_{2-6}$alkynyl, C$_{3-7}$cycloalkyl, C$_{3-7}$cycloalkyl(C$_{1-6}$)alkyl, indanyl, aryl, aryl(C$_{1-6}$)alkyl, heteroaryl, heteroaryl(C$_{1-6}$)alkyl, halogen, cyano, trifluoromethyl, nitro, —OR$^a$, —OCOR$^3$, —OSO$_2$R$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$, or —CONR$^a$R$^b$; wherein said alkyl, alkenyl, alkynyl, cycloalkyl, indanyl, aryl, heterocycloalkyl, and heteroaryl are optionally substituted by one or more groups selected from C$_{1-6}$alkyl, adamantyl, phenyl, halogen, C$_{1-6}$haloalkyl, C$_{1-6}$hydroxyalkyl, C$_{1-6}$aminoalkyl, trifluoromethyl, hydroxy, C$_{1-6}$alkoxy, aryloxy, keto, C$_{1-3}$alkylenedioxy, nitro, cyano, carboxy, C$_{2-6}$alkoxycarbonyl, C$_{2-6}$alkoxycarbonyl(C$_{1-6}$)alkyl, C$_{2-6}$alkylcarbonyloxy, arylcarbonyloxy, aminocarbonyloxy, formyl, C$_{2-6}$alkylcarbonyl, arylcarbonyl, C$_{1-6}$alkylthio, C$_{1-6}$alkylsulphinyl, C$_{1-6}$alkylsulphonyl, arylsulphonyl, —NR$^v$R$^w$, —NR$^v$COR$^w$, —NR$^v$CO$_2$R$^w$, —NR$^v$SO$_2$R$^w$, —CH$_2$NR$^v$SO$_2$R$^w$, —NHCONR$^v$R$^w$, —CONR$^v$R$^w$, —SO$_2$NR$^v$R$^w$, and —CH$_2$SO$_2$NR$^v$R$^w$, in which R$^v$ and R$^w$ independently represent hydrogen, C$_{1-6}$alkyl, aryl or aryl(C$_{1-6}$)alkyl; and R$^a$ and R$^b$ independently represent hydrogen, hydrocarbon or a heterocyclic group.

2. A compound as claimed in claim I represented by formula II and salts thereof:

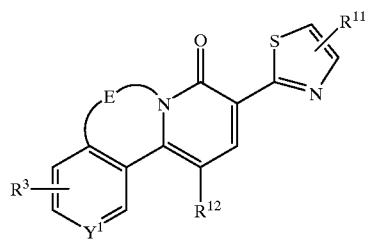

(II)

wherein

E is as defined in claim 1;

Y$^1$ represents CH or nitrogen;

R$^{11}$ represents methyl or hydroxymethyl;

R$^{12}$ represents hydrogen, halogen, aryl group, aryl(C$_{2-6}$alkenyl group, aryl(C$_{2-6}$)alkynyl group, heteroaryl group, aryloxy group, aryl(C$_{2-6}$)alkoxy group or heteroaryl(C$_{1-6}$)alkoxy group, any of which groups may be optionally substituted by one or more substituents; wherein said substituent independently is halogen, C$_{1-6}$hydroxyalkyl, C$_{1-6}$alkoxy, C$_{1-3}$alkylenedioxy, formyl or C$_{1-6}$alkylthio; and R$^{13}$ represents hydrogen, halogen, cyano, nitro, trifluoromethyl, amino, C$_{1-6}$allyl amino, di(C$_{1-6}$)alkylamino, C$_{1-6}$alkyl, C$_{1-6}$alkoxy, aryl(C$_{1-6}$)alkoxy, C$_{1-6}$alkylcarbonyl or C$_{1-6}$alkylsuphonyl.

3. A compound selected from:

11-benzyloxy-9-(4-methylthiazol-2-yl)-6,7-dihydro-5H-2,7a-diazadibenzo[α,c]cyclohepten-8-one;

11-(4-methoxyphenyl)-9-(4-methythiazol-2-yl)-6,7-dihydro-5H-2,7a-diazadibenzo[α,c]cyclohepten-8-one;

11-(3-chloro-4-methoxyphenyl)-9-(4-methylthiazol-2-yl)-6,7-dihydro-5H-2,7a-diazadibenzo[α,c]cyclohepten-8-one;

11-(4-fluorolphenyl)-9-(4-methylthiazol-2-yl)-6,7-dihydro-5H-2,7a-diazadibenzo[α,c]cyclohapten,8-one;

11-(4-hydroxymethylphenyl)-9-(4-methylthiazol-2-yl)-6,7-dihydro-5H-2,7-a-diazadibenzo[α, c]cyclohepten-8-one;

4-[9-(4-methylthiazol-2-yl)-8-oxo-6,7-dihydro-5H-2,7-a-diazadibenzo[α, c]cyclohepten-11-yl]benzaldehyde;

11-(2-methoxyphenyl)-9-(4-methylthiazol-2-yl)-6,7-dihydro-5H-2,7-a-diazadibenzo[α,c]cyclohepten-8-one;

11-(3-methoxyphenyl)-9-(4-methylthiazol-2-yl)6,7-dihydro-5H-2,7-a-diazadibenzo[α,c]cyclohepten-8-one;

9-(4-methylthiazol-2-yl)-11-phenylethynyl-6,7-dihydro-5H-2,7-a-diazadibenzo[α,c]cyclohepten-8-one;

9-(4-methylthiazol-2-yl)-11-styryl-6,7-dihydro-5H-2,7-a-diazadibenzo[α,c]cyclohepten-8-one;

9-(4-methylthiazol-2-yl)-6,7-dihydro-5H-2,7-a-diazadibenzo[α,c]cyclohepten-8-one;

11-(3,4-methylenedioxyphenyl)-9-(4-methylthiazol-2-yl)-6,7-dihydro-5H-2,7a-diazadibenzo[α,c]cyclohepten-8-one;

11-(5-fluoro-2-methoxyphenyl)-9-(4-methylthiazol-2-yl)-6,7-dihydro-5H-2,7a-diazadibenzo[α,c]cyclohepten-8-one;

11-(4-methylsulfenylphenyl)-9-(4-methylthiazol-2-yl)-6,7-dihydro-5H-2,7a-diazadibenzo[α,c]cyclohepten-8-one;

9-(4-methylthiazol-2-yl)-11-phenyl-6,7-dihydro-5H-2,7a-diazadibenzo[α,c]cyclohepten-8-one;

11-(2,5-dimethoxyphenyl)-9-(4-methylthiazol-2-yl)-6,7-dihydro-5H-2,7a-diazadibenzo[α,c]cyclohepten-8-one;

9-(4-methylthiazol-2-yl)-11-(thien-3-yl)-6,7-dihydro-5H-2,7a-diazadibenzo[α,c]cyclohepten-8-one;

11-(3,5-dichlorophenyl)-9-(4-methylthiazol-2-yl)-6,7-dihydro-5H-2,7a-diazadibenzo[α,c]cyclohepten-8-one;

9-(4-methylthiazol-2-yl)-11-(thien-2-yl)-6,7-dihydro-5H-2,7a-diazadibenzo[α,c]cyclohepten-8-one;

11-(2,4-dimethoxyphenyl)-9-(4-methylthiazol-2-yl)-6,7-dihydro-5H-2,7a-diazadibenzo[α,c]cyclohepten-8-one;

11-(benzofuran-2-yl)-9-(4-methylthiazol-2-yl)-6,7-dihydro-5H-2,7a-diazadibenzo[α,c]cyclohepten-8-one;

11-(4-fluoro-2-methoxyphenyl)-9-(4-methylthiazol-2-yl)-6,7-dihydro-5H-2,7a-diazadibenzo[α,c]cyclohepten-8-one;

11-benzyloxy-9-(4-methylthiazol-2-yl)-6,7-dihydro-5H-3,7a-diazadibenzo[α,c]cyclohepten-8-one;

11-benzyloxy-2-hydroxy-9-(4-methylthiazol-2-yl)-6,7-dihydro-5H-2,7a-diazadibenzo[α,c]cyclohepten-8-one;

11-benzyloxy-9-(4-hydroxymethylthiazol-2-yl)-6,7-dihydro-5H-2,7a-diazadibenzo[α,c]cyclohepten-8-one;

11-(2-bromobenzyloxy)-9-(4-methylthiazol-2-yl)-6,7-dihydro-5H-2,7a-diazadibenzo[α,c]cyclohepten-8-one;

11-(4-fluorobenzyloxy)-9-(4-methylthiazol-2-yl)-6,7-dihydro-5H-2,7a-diazadibenzo[α,c]cyclohepten-8-one;

11-(4-fluorobenzyloxy)-9-(4-methylthiazol-2-yl)-6,7-dihydro-5H-2,7a-diazadibenzo[α,c]cyclohepten-8-one;

9-(4-methylthiazol-2-yl)-11-phenoxy-6,7-dihydro-5H-2,7a-diazadibenzo[α,c]cyclohepten-8-one;

and salts thereof.

4. A compound selected from:

11-(2,4-dichlorophenyl)-9-(4-methylthiazol-2-yl)-6,7-dihydro-5H-2,7a-diazadibenzo[α,c]cyclohepten-8-one;

11-(3-chloro-4-fluorophenyl)-9-(4-methylthiazol-2-yl)-6,7-dihydro-5H-2,7a-diazadibenzo[α,c]cyclohepten-8-one;

11-(2-chlorophenyl)-9-(4-methylthiazol-2-yl)-6,7-dihydro-5H-2,7a-diazadibenzo[α,c]cyclohepten-8-one;

9-(4-methylthiazol-2-yl)-11-(pyridin-3-ylmethoxy)-6,7-dihydro-5H-2,7a-diazadibenzo[α,c]cyclohepten-8-one;

and salts thereof.

5. A pharmaceutical composition comprising a compound of formula I as defined in claim 1 or a pharmaceutically acceptable salt thereof in association with a pharmaceutically acceptable carrier.

6. A method for the treatment of anxiety which comprises administering to a patient in need of such treatment an effective amount of a compound of forunala I as defined in claim 1, or a phanaceudcally acceptable salt thereof.

7. A method for the treatment of convulsions which comprises administering to a patient in need of such treatment an effective amount of a compound of formula I as defined in claim 1, or a pharmaceutically acceptable salt thereof.

* * * * *